US007816370B2

(12) United States Patent
Andrieux et al.

(10) Patent No.: US 7,816,370 B2
(45) Date of Patent: Oct. 19, 2010

(54) USE OF EPOTHILONES IN THE TREATMENT OF NEURONAL CONNECTIVITY DEFECTS SUCH AS SCHIZOPHRENIA AND AUTISM

(75) Inventors: Annie Andrieux, Grenoble (FR); Didier Job, Grenoble (FR); Annie Schweitzer, Vinay (FR); Gerhard Höfle, Braunschweig (DE)

(73) Assignees: Institut National de la Sante et de la Recherche Medicale, Paris (FR); Commissariat a l'Energie Atomique, Paris (FR); Helmhaltz Zentrum Fur Infektions Forschung GmbH, Braunschweig (DE)

( * ) Notice: Subject to any disclaimer, the term of this patent is extended or adjusted under 35 U.S.C. 154(b) by 679 days.

(21) Appl. No.: 10/586,486

(22) PCT Filed: Jan. 28, 2005

(86) PCT No.: PCT/IB2005/000217

§ 371 (c)(1),
(2), (4) Date: Dec. 12, 2006

(87) PCT Pub. No.: WO2005/075023

PCT Pub. Date: Aug. 18, 2005

(65) Prior Publication Data

US 2008/0207697 A1 Aug. 28, 2008

(30) Foreign Application Priority Data

Jan. 30, 2004 (EP) .................................. 04290249

(51) Int. Cl.
*A01N 43/40* (2006.01)
*A61K 31/44* (2006.01)
(52) U.S. Cl. ........................................ 514/308; 536/7.1
(58) Field of Classification Search .................. 514/183, 514/308; 536/7.1
See application file for complete search history.

(56) References Cited

U.S. PATENT DOCUMENTS

| 6,518,421 B1 | 2/2003 | Li et al. |
| 2003/0203929 A1 | 10/2003 | Ghosh |

FOREIGN PATENT DOCUMENTS

| DE | 198 21 954 A1 | 11/1998 |
| WO | WO 98/22461 | 5/1998 |
| WO | WO 99/02514 | 1/1999 |
| WO | WO 99/07692 | 2/1999 |
| WO | WO 99/28324 A1 | 6/1999 |
| WO | WO 99/62510 A2 | 12/1999 |
| WO | WO 99/67252 | 12/1999 |
| WO | WO 00/49021 | 8/2000 |
| WO | WO 00/50423 | 8/2000 |
| WO | WO 00/66589 | 11/2000 |
| WO | WO 00/71521 A1 | 11/2000 |
| WO | WO 01/70716 A1 | 9/2001 |
| WO | WO 01/81341 A2 | 11/2001 |
| WO | WO 01/92255 A2 | 12/2001 |
| WO | WO 02/21712 A1 | 3/2002 |
| WO | WO 02/41691 A2 | 5/2002 |
| WO | WO 03/074053 A1 | 9/2003 |
| WO | WO 03/096975 A2 | 11/2003 |

OTHER PUBLICATIONS

Nicole End et al, Synthetic Epothilone analogs with Modifications in the Northern Hemisphere and the Heterocyclic Side-Chain-Synthesis and Biological Evaluation, Fourth international Electronic Conference opn Synthetic Organic Chemistry (ECSOC-4).*
Online Merck Mannuals acceesed on Oct. 26, 2009.*
Buitelaar et al. (European Child and Adolescent psychiatri 9; I/85-97, Steinkopff Verlag (2000)).*
Posey et al. ( Exp Opin. Pharmacother. (2001) 2(4):587-600).*
Nicolaou et al.; "Chemical Biology of Epothilones;" *Angewandte Chemie International Edition*; vol. 37, No. 15; pp. 2014-2045; 1998; XP002131418.
N. C. Andreasen, "Scale for the Assessment of Negative Symptoms (SANS)", Department of Psychiatry, University of Iowa College of Medicine, Iowa City, Iowa (1983) pp. 1-19.
Andreasen, Nancy C., "Schizophrenia: the fundamental questions," Brain Research Interactive, Brain Research Reviews, vol. 31, 106-112 pp, (2000).
Frankle, W. Gordon et al., "The Synaptic Hypothesis of Schizophrenia," Neuron, vol. 39, 205-216 pp, (2003).
Jamain, Stephane et al., "Mutations of the X-linked genes encoding neuroligins NLGN3 and NLGN4 are associated with autism," Nature Genetics, vol. 34, 27-29 pp, (2003).
Andrieux, Annie et al., "The suppression of brain cold-stable microtubules in mice induces synaptic defects associated with neuroleptic-sensitive behavioral disorders," Genes & Development, vol. 16, 2350-2364 pp, (2002).
Kay, Stanley R. et al., "The Positive and Negative Syndrome Scale (PANSS) for Schizophrenia," Schizophrenia Bulletin, vol. 13, No. 2, 261-276 pp, (1987).
Lindenmayer, Jean-Pierre et al., "Five-Factor Model of Schizophrenia Initial Validation," Journal of Nervous and Mental Disease, vol. 182, No. 11, 631-638 pp, (1994).
Mirnics, Karoly et al., "Analysis of complex brain disorders with gene expression microarrays: schizophrenia as a disease of the synapse," Trends in Neurosciences, vol. 24, No. 8, 479-486 pp, (2001).
Oct. 27, 2009 Notice of Opposition issued in corresponding European Application No. 05702370.7-2123/1711230.
The Merck Manual of Diagnosis and Therapy, $17^{th}$ Ed., 1999, pp. 1563-1570.
Cader et al., "Reduced Brain Functional Reserve and Altered Functional Connectivity in Patients with Multiple Sclerosis," Brain, vol. 129, 2006, pp. 527-537.
Erb et al., "Cytoarchitecture Cérébrale Dans La Schizophrénie," Psychiatr Sci Hum Neurosci, vol. 7, 2009, pp. 23-30, with English Abstract.
Wu et al., "Changes of Functional Connectivity of the Motor Network in the Resting State in Parkinson's Disease," Neuroscience Letters, vol. 460, 2009, pp. 6-10.

* cited by examiner

*Primary Examiner*—Brandon J Fetterolf
*Assistant Examiner*—Jean Cornet
(74) *Attorney, Agent, or Firm*—Oliff & Berridge, PLC

(57) ABSTRACT

The present invention is about the use of at least one epothilone or derivative thereof as an active ingredient for manufacturing a medicament for use in the treatment of disease(s) involving a neuronal connectivity defect, such as schizophrenia or autism.

23 Claims, 5 Drawing Sheets

USE OF EPOTHILONES IN THE TREATMENT OF NEURONAL CONNECTIVITY DEFECTS SUCH AS SCHIZOPHRENIA AND AUTISM

The present invention relates to the use of epothilones for manufacturing a medicament for use in the treatment of psychotic disorders thought to be associated with neuronal connectivity defects in the absence of obvious anatomical, degenerative, or proliferative anomalies.

Psychotic disorders are disorders that are predominantly characterized by an impairment of mental functioning to the extent that it interferes grossly with an individual's ability to meet the ordinary demands of life.

Psychotic disorders currently thought to result from disorders in neuronal connectivity include, and are not limited to, schizophrenia, schizophreniform disorder, schizoaffective or delusional disorder, and autism (Andreassen N C, Brain Res. Rev. 2000; 31:106-12; Francke et al., Neuron, 2003, 39, 205-216; Jamain et al, Nature Genetics, 2003, 34, 27-28.1).

Schizophrenia is any of a group of psychotic disorders usually characterized by withdrawal from reality, illogical patterns of thinking, delusions and hallucinations and accompanied in varying degrees by other emotional, behavioral or intellectual disturbances. A lifelong chronic mental illness, schizophrenia exhibits positive and negative symptoms, with an onset in young adulthood and deterioration from the previous level of functioning. Positive symptoms reflect a distortion or excess of normal functions (eg, disorganized speech, delusions, and hallucinations). Negative symptoms, on the other hand, reflect a restricted range of normal behavior and emotions (eg, apathy, paucity of speech and incongruity or flattening of emotional responses). Schizophrenia can be presented in various forms depending on the symptoms and signs. The varieties of schizophrenia include paranoid schizophrenia, hebephrenic schizophrenia, catatonic schizophrenia, and undifferentiated schizophrenia as well as post-schizophrenic depression, residual schizophrenia, simple schizophrenia and unspecified schizophrenia.

Neuroleptic agents or drugs (i.e. "neuroleptics"), also called anti-psychotics or major tranquilizers remain the treatment of choice for schizophrenia, certain organic central nervous system disorders, mental illnesses, and associated psychotic processes today. Currently, it is estimated that over 95% of schizophrenics are chronically maintained on neuroleptics. All known neuroleptics are dopaminergic blockers, having pharmacological actions similar to the action of chlorpromazine, an aliphatic phenothiazine derivative also known as Thiorazine.

Although the known anti-psychotic drugs have clear efficacy in the treatment of mental illness, they do not cure all symptoms and have a variety of side effects.

Figure 1:
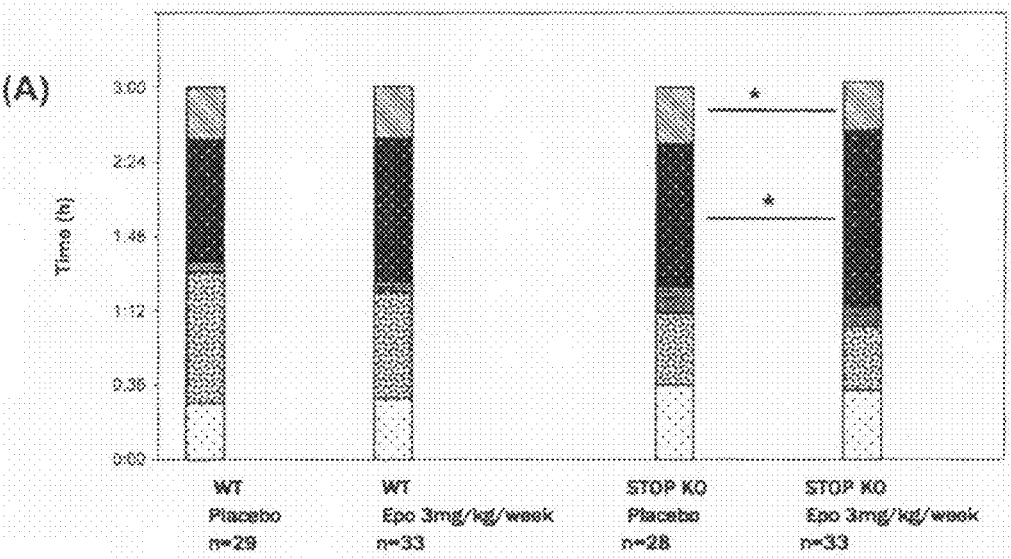
FIG. 1 shows two graphs charting activities of mice treated or not with 3 mg/kg/week of epothilone D. The upper panel (A) indicates the amount of time spent in each activity, and lower panel (B) indicates the number of occurrences of each activity.
Figure 1:
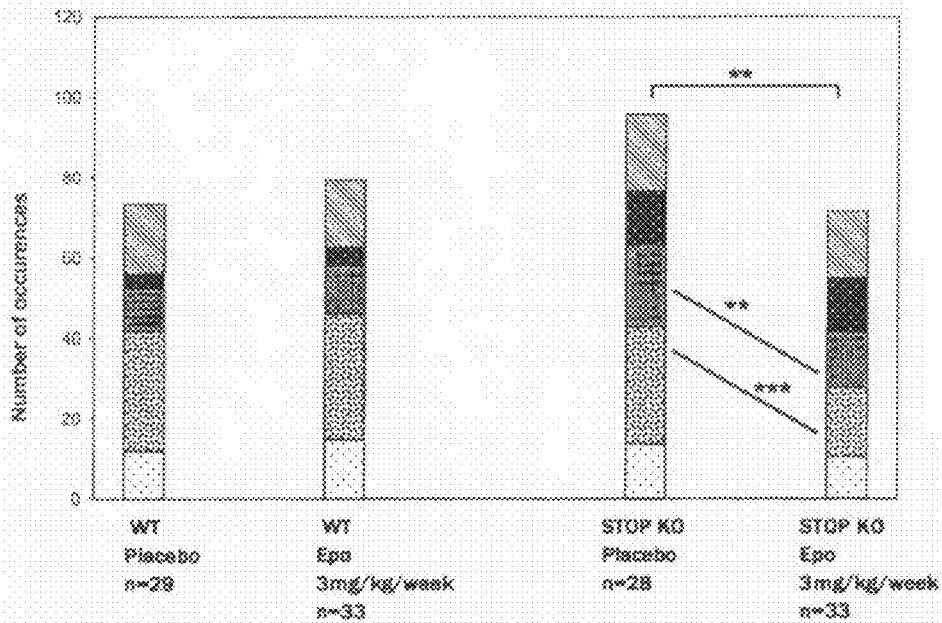

The invention derives from the discovery that epothilones can alleviate schizophrenia-related behavioural disorders in an animal model termed STOP deficient mice (Andrieux et al.: Genes Dev. 2002 Sep. 15; 16(18): 2350-64).

The natural products Epothilones A and B as well as some of their synthetic derivatives have recently found interest in connection with the treatment of cancer. Thus, WO 98/22461, WO 99/07692, DE 198 21954, WO 99/02514, WO 99/67252, WO 00/50423, WO 02/21712, WO 00/66589, WO 01/081341, WO 00/49021 and US 2003/0 203 929 deal with the synthesis of epothilone derivatives and for some of them with their use in the treatment of cancers. WO 03/074053 relates more specifically to the use of some epothilone derivatives to treat diseases involving degenerative or hyperproliferative processes, such as brain tumor, Alzeihmer's disease, multiple sclerosis and primary or secondary brain tumors.

A beneficial effect of epothilones has now been demonstrated in STOP deficient mice which display neuronal connectivity defects not associated with any detectable anatomical, degenerative or proliferative anomalies.

It has been observed, notably, that administration of epothilone D to STOP KO mice resulted in a decrease in the total number of shifts between activities indicating an alleviation of the activity fragmentation, characterizing untreated STOP deficient mice.

Furthermore, the maternal behaviour of STOP deficient female mice treated with epothilone D was re-established in the extent to which it was compatible with pup survival.

It has been observed that after D epothilone treatment, the synaptic vesicle density was increased in STOP KO mice by about 20% such an effect being similar to that obtained after a long-term neuroleptic treatment.

Accordingly, the invention provides alternative therapies for treating some Central Nervous System (CNS) disorders and mental illness, associated with neuronal connectivity defect, particularly schizophrenia and autism, said defects being not associated with any detectable anatomical, degenerative or proliferative anomalies.

According to a first aspect, the present invention is directed to the use of at least one epothilone or derivative thereof as an active ingredient, in particular in a therapeutically effective amount, for manufacturing a medicament for use in the treatment of disease(s) involving a neuronal connectivity defect.

In particular, the present invention is directed to the use of at least one epothilone or derivative thereof as an active ingredient, in particular in a therapeutically effective amount, for manufacturing a medicament for use in the treatment of schizophrenia and/or autism.

According to a second aspect, the present invention is directed to a method of treatment of disease(s) involving a neuronal connectivity defect comprising administering to an individual in need thereof a therapeutically effective amount of at least one epothilone or derivative thereof, in particular as defined according to the invention.

An embodiment of the method of the present invention comprises administering to an individual a therapeutically effective amount of at least one epothilone or derivative thereof, in particular as defined according to the instant invention, in a pharmaceutical composition comprising at least a pharmaceutically acceptable carrier.

Another embodiment of the method of the present invention comprises administering to an individual a therapeutically effective amount of at least one epothilone or derivative thereof, in particular according to the invention or a pharmaceutical composition thereof in combination with one or more agents useful in preventing or treating psychotic or psychiatric disorders, in particular such as neuroleptics.

As used herein, the term "disease associated with neuronal connectivity defect" refers to mental diseases currently thought to involve neuronal connectivity disorder, in the absence of obvious anatomical, proliferative or degenerative anomaly. Examples of such disorders include particularly schizophrenia and autism. In particular, the diseases considered according to the invention are different from progressive dementing disorders like Alzheimer, which involve neuronal degeneration.

As used herein, the term "schizophrenia" refers to a psychiatric disorder that includes at least two of the following: delusions, hallucinations, disorganized speech, grossly disorganized or catatonic behaviour, or negative symptoms. Patients can be diagnosed as schizophrenic using the DSM-IV criteria (APA, 1994, *Diagnostic and Statistical Manual of Mental Disorders* (Fourth Edition), Washington, D.C.).

"Negative" symptoms of schizophrenia include affect blunting, anergia, alogia and social withdrawal, which can be measured using SANS (the Scales for the Assessment of Negative Symptoms; see Andreasen, 1983, *Scales for the Assessment of Negative Symptoms* (SANS), Iowa City, Iowa).

"Positive" symptoms of schizophrenia include delusion and hallucination, which can be measured using PANSS (the Positive and Negative Syndrome Scale; see Kay et al., 1987, Schizophrenia Bulletin 13:261-276).

"Cognitive" symptoms of schizophrenia include impairment in obtaining, organizing, and using intellectual knowledge which can be measured by the Positive and Negative Syndrome Scale-cognitive subscale (PANSS-cognitive subscale) (Lindenmayer et al., 1994, J. Nerv. Ment. Dis. 182:631-638) or with cognitive tasks such as the Wisconsin Card Sorting Test.

As used herein, the term "autism" refers to a state of mental introversion characterized by morbid self-absorption, social failure, language delay, and stereotyped behavior. Patients can be diagnosed as suffering from autism by using the DSM-IV criteria.

"Treating" or "treatment" as used herein refers to the treatment of a disease in an individual, which disease is associated with neuronal connectivity defect and includes:
(i) inhibiting the disease, i.e., arresting its development; or
(ii) relieving the disease, i.e., alleviating symptoms caused by the disease.

According to one embodiment, the used epothilone may be derivatives of epothilones of following formula (I):

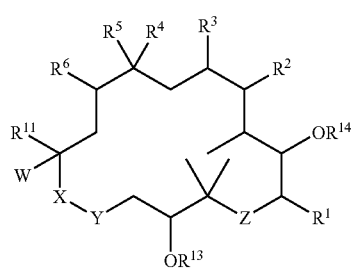

(I)

wherein:
$R^1$ represents H, alkyl, alkenyl or alkynyl in $C_1$-$C_6$, aryl in $C_6$-$C_{10}$, aralkyl in $C_7$-$C_{15}$,
$R^2$, $R^3$ represents each H or form together C=C double bond,
$R^4$ represents H, $C_1$-$C_6$-alkyl in particular $CH_3$, fluoro substituted $C_1$-$C_6$ alkyl in particular $CF_3$ or $CFH_2$,
$R^5$ and $R^6$ form a C=C double bond or a three membered ring including O, S, $NR^7$, $CR^8R^9$ with $R^7$ being C(O)$R^{10}$, $SO_2R^{10}$ and $R^8$, $R^9$, $R^{10}$ being independently H, halogen, $C_1$-$C_6$ alkyl, $C_6$-$C_{10}$ aryl, $C_7$-$C_{15}$ alkaryl,
$R^{11}$ being H, $C_1$-$C_6$ alkyl, $C_6$-$C_{10}$ aryl, $C_7$-$C_{15}$ alkaryl, and in particular H,
W represents $C(R^{12})$=CH, $C(R^{12})$=C($CH_3$), $C(R^{12})$=CF or a bicyclic aromatic/heteroaromatic radical preferably a 2-methylbenzothiazol-5-yl radical, or a 2-methylbenzoxazol-5-yl radical or a quinolin-7-yl radical, with $R^{12}$ representing a heteroaromatic radical, preferably a 2-pyridinyl, a 2-substituted thiazol-4-yl or a 2-substituted oxazol-4-yl radical with substitution in 2-position by $C_1$-$C_6$-alkyl, pseudohalogen like CN or $N_3$, S—$C_1$-$C_4$-alkyl, O—$C_1$-$C_6$-alkyl, or $C_1$-$C_6$-alkyl substituted by OH, amino, halogen, pseudohalogen such as —NCO, —NCS, —$N_3$, O—($C_1$-$C_6$)-acyl, O—($C_1$-$C_6$)-alkyl or O-benzoyl,
X—Y represents O—C(=O), O—$CH_2$, $CH_2$—O, $CH_2$—C(=O),
Z represents C=O, S, S=O, $SO_2$,
$R^{13}$ and $R^{14}$ represents independently from each other H, $C_1$-$C_6$-alkyl, (CO)$R^{15}$ or $C_{1-4}$-trialkylsilyl, with $R^{15}$ being H, $C_1$-$C_6$-alkyl, fluoro substituted $C_1$-$C_6$-alkyl, and pharmaceutically acceptable salts thereof.

According to one embodiment, the used epothilone may be derivatives of epothilones of following formula (II):

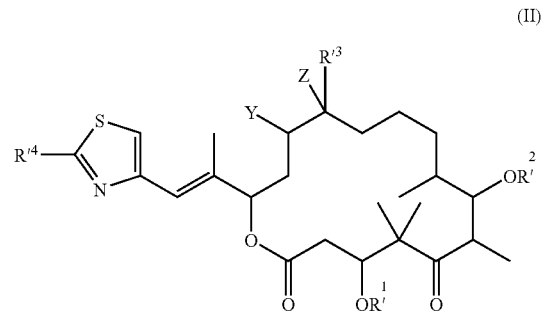

(II)

wherein:
$R'^4$ represents an $C_1$-$C_6$-alkyl or substituted $C_1$-$C_6$-alkyl with substituents as F, Cl, Br or I, pseudohalogen such as —NCO, —NCS, —$N_3$, $NH_2$, OH, O—($C_1$-$C_6$)-acyl, O—($C_1$-$C_6$)-alkyl or O-benzoyl,
$R'^1$ and $R'^2$ are independently from each other H, $C_1$-$C_6$-alkyl, (CO)$R'^5$ with $R'^5$ being H, $C_1$-$C_6$-alkyl, $C_1$-$C_6$-fluoroalkyl or $C_{1-4}$-trialkylsilyl,
$R'^3$ represents H, $C_1$-$C_6$-alkyl, halogen substituted $C_1$-$C_6$-alkyl, and
Y and Z form either a C=C double bond or are the O atom of an epoxide and pharmaceutically acceptable salts thereof.

Depending on the nature of the various substituents, the compounds of formula (I) and (II) may have several asymmetric carbon atoms. Unless otherwise mentioned or indicated, the chemical designation of compounds denotes the mixture of all possible stereochemically isomeric forms, said mixtures containing all diastereomers and enantiomers of the basic molecular structure.

The term addition salt as used hereinabove also comprises the solvates which the compounds of formula (I) and (II) are able to form and said solvates are meant to be included within the scope of the present invention. Examples of such solvates are e.g., the hydrates, alcoholates and the like.

As used therein, the term "alkyl" includes straight chained and branched hydrocarbon groups containing the indicated number of carbon atoms, typically methyl, ethyl, and straight-chain and branched propyl and butyl groups. Unless otherwise indicated, the hydrocarbon group can obtain up to 16 carbon atoms. The term "alkyl" includes "bridged alkyl". Alkyl groups can be substituted, for example, with hydroxy (OH), halogen, aryl, heteroaryl, cycloalkyl, heterocycloalkyl, cycloalkenyl, heterocycloalkenyl, amino ($N(R^b)_2$), and sulfonyl ($SO_2R^b$), wherein $R^b$ is selected from the group consisting of hydro, $C_1$-$C_6$alkyl, cycloalkyl, aryl, and $SO_2C_1$-$C_6$-alkyl, or two $R^b$ groups are taken together to form a 5- or 6-membered ring.

The terms "cycloalkyl" and "cycloalkenyl" are defined as a cyclic $C_{3-7}$ hydrocarbon group, e.g., cyclopropyl, cyclobutyl, cyclohexyl, cyclohexenyl, cyclopentenyl, and cyclopentyl. "Heterocycloalkyl" and "heterocycloalkenyl" are defined similarly as cycloalkyl except the ring contains one to three hereroatoms selected from the group consisting of oxygen, nitrogen, and sulphur. Cycloalkyl and heterocycloalkyl groups are saturated ring systems, and cycloalkenyl and heterocycloalkenyl are partially unsaturated ring systems, all optionally substituted with, for example, one to three groups, independently selected from $C_{1-4}$-alkyl, $C_{1-3}$-alkylene-OH, $C_{1-3}$alkylene-$N(R^a)_2$, $NH_2$, oxo (=O), aryl, and OH.

The term "halogen" is defined herein to include fluoro, bromo, chloro, and iodo.

The term "aryl", alone or in combination, is defined herein as a monocyclic or bicyclic aromatic group, e.g., phenyl or naphtyl. Unless otherwise indicated, an "aryl" group can be unsubstituted or substituted. Exemplary aryl groups include phenyl, naphthyl, tetrahydronaphthyl, chlorophenyl, methylphenyl, methoxyphenyl, trifluoromethylphenyl, nitrophenyl, 2,4-methoxychlorophenyl, and the like.

The term "heteroaryl" is defined herein as a monocyclic or bicyclic ring system containing at least one nitrogen, oxygen, or sulfur atom in an aromatic ring, and that can be unsubstituted or substituted. Examples of heteroaryl groups include, but are not limited to thienyl, furyl, pyridyl, oxazolyl, quinolyl, isoquinolyl, indolyl, triazolyl, isothiazolyl, isoxazolyl, imidizolyl, benzothiazolyl, pyrazinyl, pyrimidinyl, thiazolyl, and thiadiazolyl.

The term "alkoxy" is defined as —OR, wherein R is alkyl, including cycloalkyl.

The term "acyl" is defined as —CO—R, wherein R is alkyl, including cycloalkyl.

Epothilones of formula (I) and (II) are especially interesting as they appear to offer relief of both the positive and negative symptoms of schizophrenia. Further the present compounds also appear to be useful therapeutic agents for combating autism.

More particularly, the epothilone is at least a derivative of formula II wherein $R^{r1}$, $R^{r2}$, $R^{r3}$ represent independently from each other, H, $C_1$-$C_6$-alkyl in particular $CH_3$, $C_1$-$C_6$ perfluoroalkyl in particular $CF_3$ and Y and Z form together a C=C double bond or are together the O atom of an epoxide.

According to another specific embodiment, the used epothilones include at least the natural epothilones A or B of following formula:

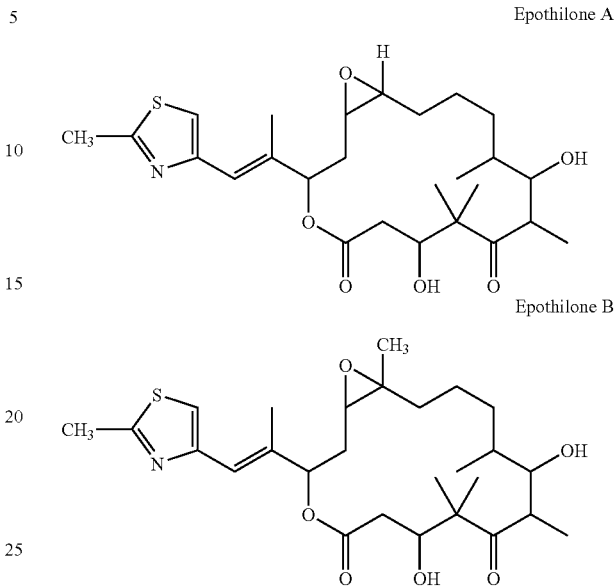

and pharmaceutically acceptable salts thereof.

According to another specific embodiment, epothilones may be synthetic epothilone C, D, E or F of the following formula:

Epothilone F

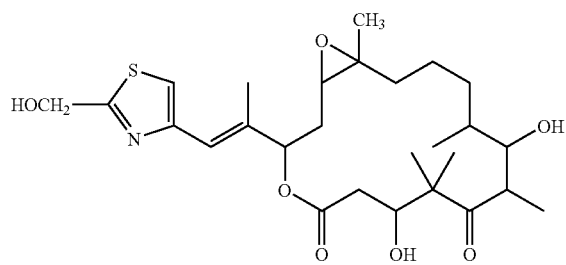

and in particular the epothilone D or derivative or salt thereof.

According to another specific embodiment, epothilone may be synthetic epothilone of following formula:

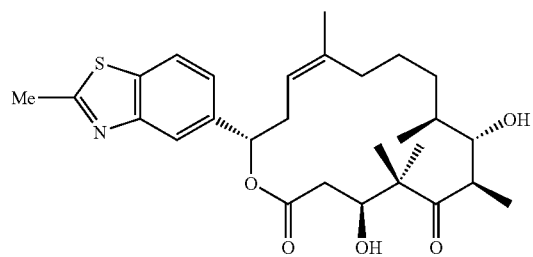

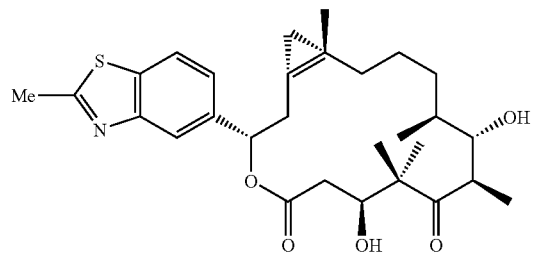

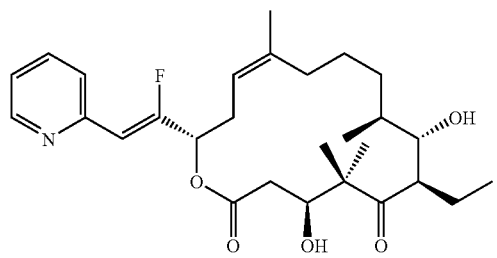

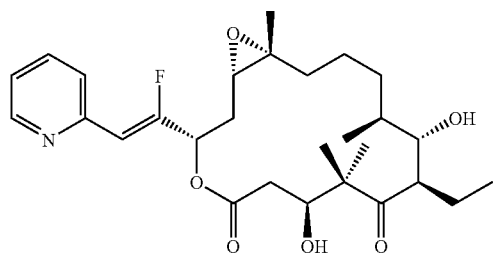

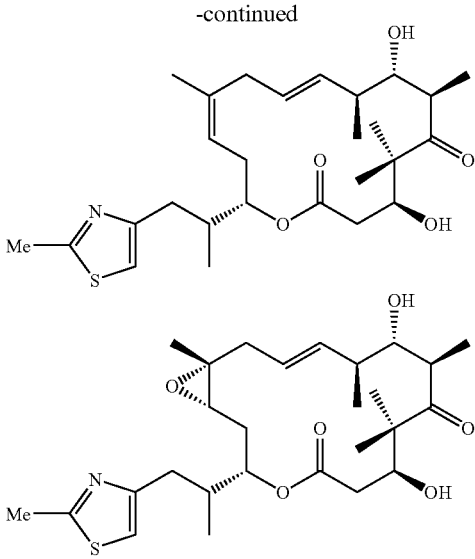

The term "therapeutically effective amount" as used herein refers to that amount in epothilone which, when administered to an individual in need thereof, is sufficient to provide efficient treatment, as defined below, for diseases associated with neuronal connectivity defect.

Naturally, the amount which constitutes a "therapeutically effective amount" will vary depending on the compound, the disease and its severity, and the age of the human to be treated, that can be determined routinely by one ordinary skill in the art having regard to his own knowledge and to this disclosure.

For example, the therapeutically effective amount in epothilone and in particular of a compound selected from the group consisting of Formula (I) or (II) may be from about 0.01 mg/Kg/dose to about 100 mg/Kg/dose. Preferably, the therapeutically effective amount may be from about 0.01 mg/Kg/dose to about 25 mg/Kg/dose. More preferably, the therapeutically effective amount may be from about 0.01 mg/Kg/dose to about 10 mg/Kg/dose. Most preferably, the therapeutically effective amount may be from about 0.01 mg/Kg/dose to about 5 mg/Kg/dose. Therefore, the therapeutically effective amount of the active ingredient contained per dosage unit (e.g., tablet, capsule, powder, injection, suppository, teaspoonful and the like) as described herein may be from about 1 mg/day to about 7000 mg/day for a subject, for example, having an average weight of 70 Kg.

For the use according to the invention, the epothilone can be formulated by methods known in the art. Compositions for the oral, rectal, parenteral or local application can be prepared in the form of tablets, capsules, granulates, suppositories, implantages, sterile injectable aqueous or oily solutions, suspensions or emulsions, aerosols, salves, creams, or gels, retard preparations or retard implantates. The epothilone may also be administered by implantable dosing systems. In particular the epothilone is formulated for perfusion.

The pharmaceutical active epothilone can thus be mixed with adjuvants known in the art, such as gum Arabic, talcum, starch, mannitol, methyl cellulose, lactose, surfactants such as Tweens® or Myrj®, magnesium stearate, aqueous or non-aqueous carriers, paraffin derivatives, wetting agents, dispersing agents, emulsifiers, preservatives, and flavours.

An epothilone according to the invention or a pharmaceutical composition thereof may be administered by any conventional route of administration including, but not limited to oral, pulmonary, intraperitoneal (ip), intravenous (iv), intramuscular (im), subcutaneous (sc), transdermal, buccal, nasal, sublingual, ocular, rectal and vaginal. In addition, administration directly to the nervous system may include, and are not limited to, intracerebral, intraventricular, intracerebroventricular, intrathecal, intracisternal, intraspinal or peri-spinal routes of administration by delivery via intracranial or intravertebral needles or catheters with or without pump devices. It will be readily apparent to those skilled in the art that any dose or frequency of administration that provides the therapeutic effect described herein is suitable for use in the present invention.

The invention is further illustrated by the following examples and figures:

FIG. 1:

It reports mouse activities treated or not with 3 mg/kg/week of epothilone D (sleeping, feeding, grooming, walking and remaining still while awake) that were video-recorded during 3 h. Upper panel (A) reports time spent in each different activity (calculated for each mouse and averaged). Lower panel (B) number of occurrences of each activity (calculated for each mouse and averaged).

*$p \leq 0.05$, $p \leq 0.01$, *$p \leq 0.001$, ANOVA.

FIG. 2:

It reports mouse activities (sleeping, feeding, grooming, walking and remaining still while awake) that were treated or not treated with epothilone D at a dose of 4 mg/kg/week. The activities are video-recorded during 3 h. Left Panels: number of occurrences of each activity (calculated for each mouse and averaged, mean ±s.e.m). Right Panels: time spent in each different activity (calculated for each mouse and averaged, mean ±s.e.m). Group sizes were: WT placebo: n=9; WT epothilone D: n=10; STOP KO placebo: n=10; STOP KO epothilone D: n=10

*$p \leq 0.05$, $p \leq 0.025$, *$p < 0.01$, ANOVA.

FIG. 3:

It reports nesting capacity of mice treated or not with a dose of epothilone D ranging from 0.3 mg/kg/week to 3 mg/kg/week. Tissue use score (T: 0-2), Nest building score (N: 0-2), Number of retrieved pups (R: 0-3=and global score (T+N+R) were calculated for each mouse and averaged (mean ±s.e.m.).

*$p \leq 0.05$, $p \leq 0.01$, *$p \leq 0.001$, ANOVA.

FIG. 4:

It reports the nesting capacity of mice treated or not with a dose of epothilone D at a dose of 4 mg/kg/week. Tissue use score (T: 0-2), Nest building score (N: 0-2), Number of retrieved pups (R: 1-3) and global score (T+N+R) were calculated for each mouse and averaged (mean ±s.e.m). Group sizes: as in FIG. 2.

$p \leq 0.05$, $p \leq 0.025$, *$p \leq 0.01$, ANOVA

FIG. 5:

It reports the quantitative analysis of synaptic vesicle density in CA1 hippocampal synapses of mice treated or not with epothilone D 3 mg/kg/week or with neuroleptics (0.5 mg/kg/day haloperidol and 5 mg/kg/day chlorpromazine, in drinking water, from birth to adulthood). Synaptic vesicle density, calculated as the ratio of the number of vesicle/nerve terminal surface (after subtraction of the surface area occupied by mitochondria). Results (means +/−s.e.m.) are shown for pooled 75 measurements from five wild type mice and from five STOP KO mice either untreated or treated with Epothilone D. For neuroleptic control experiments, results (means +/−s.e.m.) are shown for pooled 75 measurements from three STOP KO mice either untreated or treated with neuroleptics.

***$p \leq 0.001$, t-test.

MATERIAL AND METHODS

Epothilone D has been tested in STOP deficient mice. These mice (STOP KO) display neuronal connectivity defects, with synaptic defects affecting both long- and -short term synaptic plasticity with a large depletion of synoptic vesicle pool within the hippocampal synapses (WT: 280 synaptic vesicles/$\mu m^2$; STOP KO: 150 synaptic vesicles/$\mu m^2$). The synaptic defects are associated with severe behavioral disorders. Behavioral disorders in STOP KO mice are alleviated by long-term treatment with neuroleptics. STOP KO mice are currently considered as a valuable animal model for study of the origin and treatment of mental diseases thought to result from a disease of the synapse, such as schizophrenia (Mirmics et al., Trends Neurosci., 2001, 24, 479-486).

Whereas behavioral defects in STOP KO mice are complex, these defects ultimately result in conspicuous alterations of spontaneous behaviour, with a fragmented activity characterized by frequent shifts between activities, and in severe deficits affecting tasks related to nurturing, such as nest building and pup retrieving. (Andrieux et al., Genes Dev. 2002 Sep. 15; 16(18):2350-64). Both spontaneous activity and maternal behaviour were examined for test of epothilone effect.

Spontaneous activity (male and female) was recorded and quantified during a three hours period of time, as in Andrieux et al., Genes Dev. 2002 Sep. 15; 16(18):2350-64. Five activities were considered: feeding, remaining still without sleeping, walking, grooming and sleeping. For each activity, the total time spent doing the activity and the number of distinct sequences of activity, were determined.

For maternal behaviour, STOP deficient or control wild type (WT) female mice, nulliparous, 8 weeks old, were treated either with a placebo (carrier alone), or with epothilone D.

The maternal behaviour of treated and untreated mice was monitored by assaying the mouse ability to build a nest and to retrieve pups For assessment of nesting capacity, the tested mouse was placed in a 240×240×120 mm cage containing litter and provided with a Kleenex tissue folded in 4 (final dimensions, 100×100 mm). After 60 hours, the mouse ability to use the paper and to build a nest was scored as follows:

Tissue use score: 0, the Kleenex tissue remained folded; 1, the tissue has been unfolded but not shredded; 2 the tissue was shredded.

Nest building score: 0, no attempt to build a nest; 1, primitive flat nest of uncontrolled shape; 2, true nest, the paper is mixed with litter to form a circular nest, less than 80 mm in diameter.

For assessment of retrieving: following the nest building test, mice were trained and assessed for pup retrieving as in Andrieux et al. (Genes Dev. 2002 Sep. 15; 16(18):2350-64. Retrieving was scored as the number of pups retrieved (0 to 3).

Finally a global score for nesting and retrieving capacity (TNR) was determined for each mouse, by adding the tissue use, nest building, and pup retrieving scores (maximal score for TNR is 7).

The effect of epothilones treatment was also analyzed on the pool of synaptic vesicles.

Hippocampus was dissected out from transcardially fixed mice, sliced and embedded in Epon. To determine the surface density of synaptic vesicles, a total of cross sections of 75 synapses made of hippocampal CA1 region were photographed randomly, and the numbers of synaptic vesicles in each nerve pre-terminal were counted on the electron micrographs. Synaptic vesicles density of STOP KO mice following long term neuroleptic treatment (0.5 mg/kg/day haloperidol and 5 mg/kg/day chlorpromazine, in drinking water, from birth to adulthood) was also examined using the same protocol.

In a first series of experiments, epothilone D was injected intra-peritoneally, once a week, at either 0.3 mg/kg/week or 3 mg/kg/week for at least 8 weeks. The drug was diluted at a final concentration of 0.3 mg/ml in water, from a 50 mg/ml stock solution in DMSO.

In a second series of experiments, epothilone D was injected intra-peritoneally, in two injections a week, at a total dose of 4 mg/kg/week, for 8 weeks. The drug was diluted at a final concentration of 0.2 mg/ml in water, from a 50 mg/ml stock solution in DMSO.

EXAMPLE I

Effect of Epothilone D on Spontaneous Activity

Among 61 STOP KO mice, 28 were treated with placebo injections, 33 with 3 mg/kg/week of epothilone D. Among 62 WT mice, 29 were treated with placebo injections, 33 with 3 mg/kg/week of epothilone D.

In STOP deficient mice, epothilone D treatment with 3 mg/kg/week caused a decrease in the total time spent grooming and an increase in the total time spent sleeping (FIG. 1-A). Epothilone D treatment also decreased the total number of shifts between activities (FIG. 1-B), reducing both the number of walking and remaining still while awake sequences. These results obtained on a large number of animals including both males and females indicate an alleviation of the activity fragmentation that is characteristic of untreated STOP KO mice (Andrieux et al., Genes Dev. 2002 Sep. 15; 16(18):2350-64).

In another series of experiments, among 19 STOP KO mice, 9 were treated with placebo injections, 10 with 4 mg/kg/week epothilone D. Among 20 WT mice, 10 were treated with placebo injections and 10 with 4 mg/kg/week epothilone D.

Figure 2:
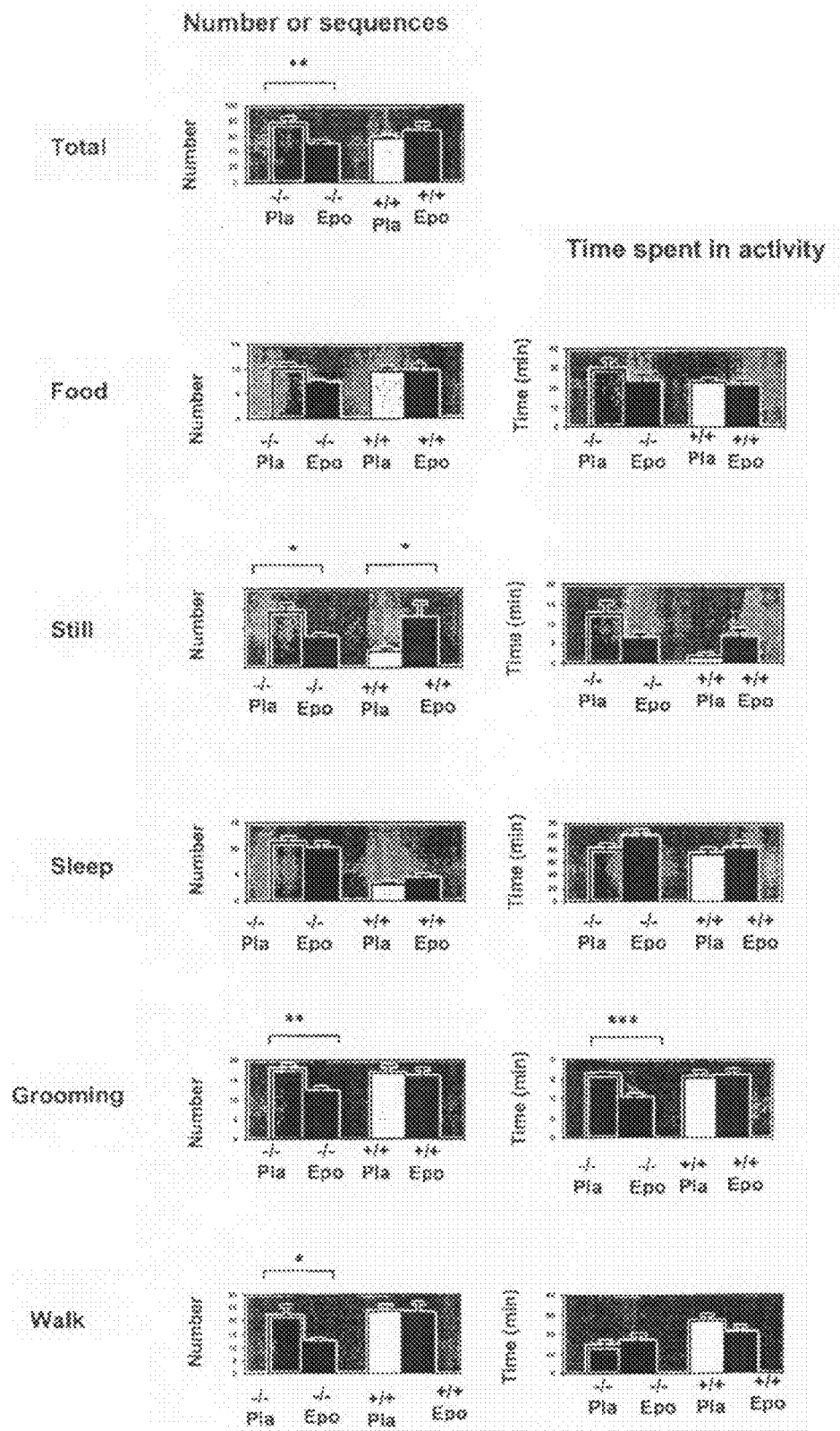
FIG. 2 shows graphs indicating the amount of time spent in various activities and the number of occurrences for each activity for mice that were treated or not treated with epothilone D at a dose of 4 mg/kg/week.

In STOP deficient mice, epothilone D treatment with 4 mg/kg/week for 8 weeks caused a remarkable decrease in the total number of shifts between activities (see FIG. 2). This decrease in number concerned the number of walking, and grooming sequences, whereas the number of sleeping and feeding sequences remained unaffected. The total time spent grooming was also highly significantly diminished by epothilone treatment. Finally, epothilone treatment tended to diminish the time spent remaining still without sleeping, and to increase the time spent sleeping. Again, these results indicate a conspicuous alleviation of the activity fragmentation that is characteristic of untreated STOP deficient mice (Andrieux et al., Genes Dev. 2002 Sep. 15; 16(18):2350-64), with a trend to diminish abnormal activities such as remaining still without sleeping, or activities that can be stereotypic such as grooming, and to increase sleeping which is deficient in untreated STOP KO mice (Andrieux et al., Genes Dev. 2002 Sep. 15; 16(18):2350-64).

EXAMPLE II

Effect of Epothilone D on Maternal Behaviour

The maternal behaviour of untreated and treated mice was monitored by assaying mouse ability to build a nest and to retrieve pups. Experiments were performed at 3 concentrations of epothilone D (4 mg/kg/week, 3 mg/kg/week and 0.3 mg/kg/week).

Among 69 STO KO mice, 2 groups of 17 were treated with placebo injections, 17 were treated with 3 mg/kg/week of epothilone, and 18 were treated with 0.3 mg/kg/week of epothilone. Among 34 WT mice, 17 were treated with placebo injections, and 17 were treated with 3 mg/kg/week of epothilone.

Figure 3:
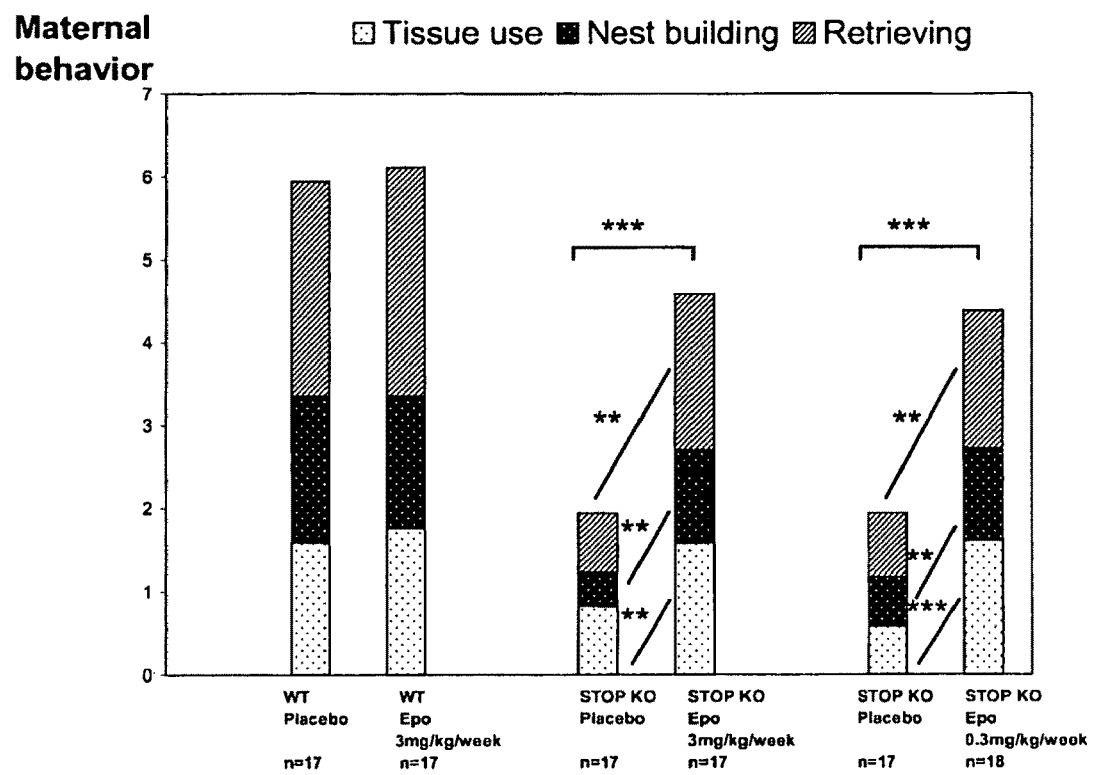
FIG. 3 is a graph indicating the nesting capacity of mice treated or not with a dose of epothilone D ranging from 0.3 mg/kg/week to 3 mg/kg/week.

Epothilone treatment at both 3 mg/kg/week and 0.3 mg/kg/week improved the paper use score, the nest building score, and the pup retrieving score inducing a highly significant increase in the TNR score (FIG. 3). Epothilone treatment at both 3 mg/kg/week and 0.3 mg/kg/week thus had a remarkable beneficial effect on nurturing-related tasks that are strongly deficient in untreated STOP KO mice.

The epothilone treatment has been then tested whether it could induce pup survival in STOP KO mothers. Nine STOP KO mice treated with Epothilone D at 0.3 mg/kg/week and eight untreated females were mated the pups survival were analysed after delivery. Remarkably, in three out of the nine STOP KO females subjected to epothilone D treatment, nurturing improvement was sufficient to permit pup survival with ratios of surviving pups to newborns of 5/6, 6/6, 5/6, for the three mice. Accordingly with previous observations (Andrieux et al., Genes Dev. 2002 Sep. 15; 16(18):2350-64) in the absence of treatment, pup survival did not occur in the progeny from STOP KO mothers. Pups survival observed after epothilone D treatment can be compared to the occurrence of pup survival in long-term neuroleptic treated STOP KO mice where the pups survival were observed in four out of seven STOP KO females (ratios of surviving pups to newborns of 3/11, 4/8, 2/4, 1/5, for the four mice). These results indicate a remarkable capacity of epothilone D in re-establishing maternal abilities compatible with pup survival in STOP KO mice.

In another series of experiments, among 19 STOP KO mice, 9 were treated with placebo injections, 10 with 4 mg/kg/week epothilone D and as control, among 20 WT mice, 10 were treated with placebo injections and 10 with 4 mg/kg/week epothilone D.

Figure 4:
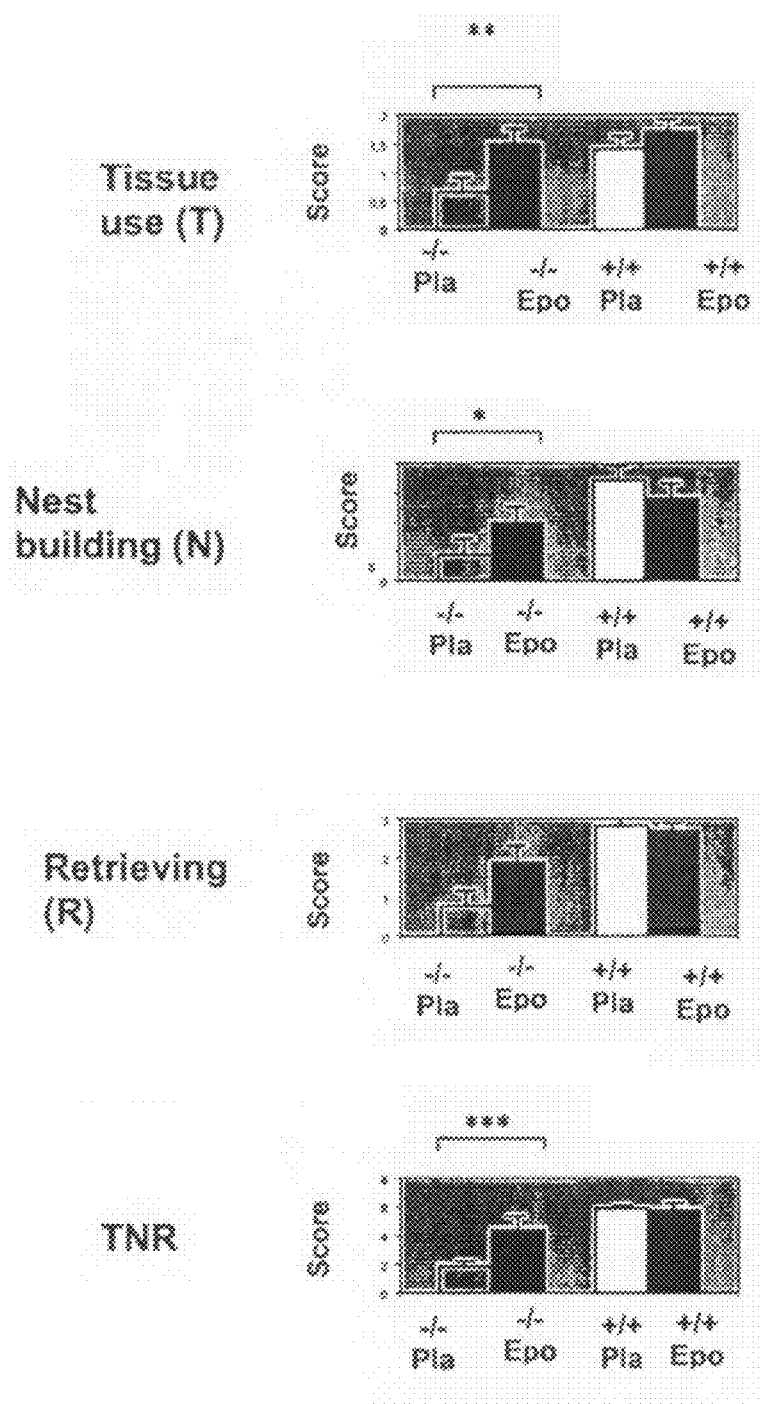
FIG. 4 shows graphs indicating the nesting capacity of mice treated or not with a dose of epothilone D at a dose of 4 mg/kg/week.

In STOP deficient mice, epothilone treatment at 4 mg/kg/week strongly improved the paper use score, the nest building score, and tended to improve the pup retrieving score (FIG. 4). There was a highly significant increase in the TNR score, which rose from 1.16 to 4.4, upon epothilone treatment, in STOP KO mice (FIG. 4). The treatment thus had a remarkable beneficial effect on nurturing-related tasks that are strongly deficient in untreated STOP KO mice.

In both example I and example II, epothilone treatment had no significant effect on the recorded activities or on nurturing-related behaviours in WT mice, with the exception of a significant increase in the number of sequences of stillness in example II (FIG. 2). However, the observation of a single significant difference among multiple comparisons is compatible with random fluctuations. Altogether, results indicate that epothilones have little or no psychotropic effects in WT mice.

Taken together, these results show that epothilone treatment can alleviate behavioural disorders in an animal model of psychiatric disease involving connectivity disorders while unaffecting WT mice.

EXAMPLE III

Effect of Epothilones an Hippocampal Synaptic Vesicle Density

For this study hippocampal sections from 5 WT and 5 STOP KO mice either untreated or treated with epothilone D at 4 mg/kg/week were used.

Figure 5:
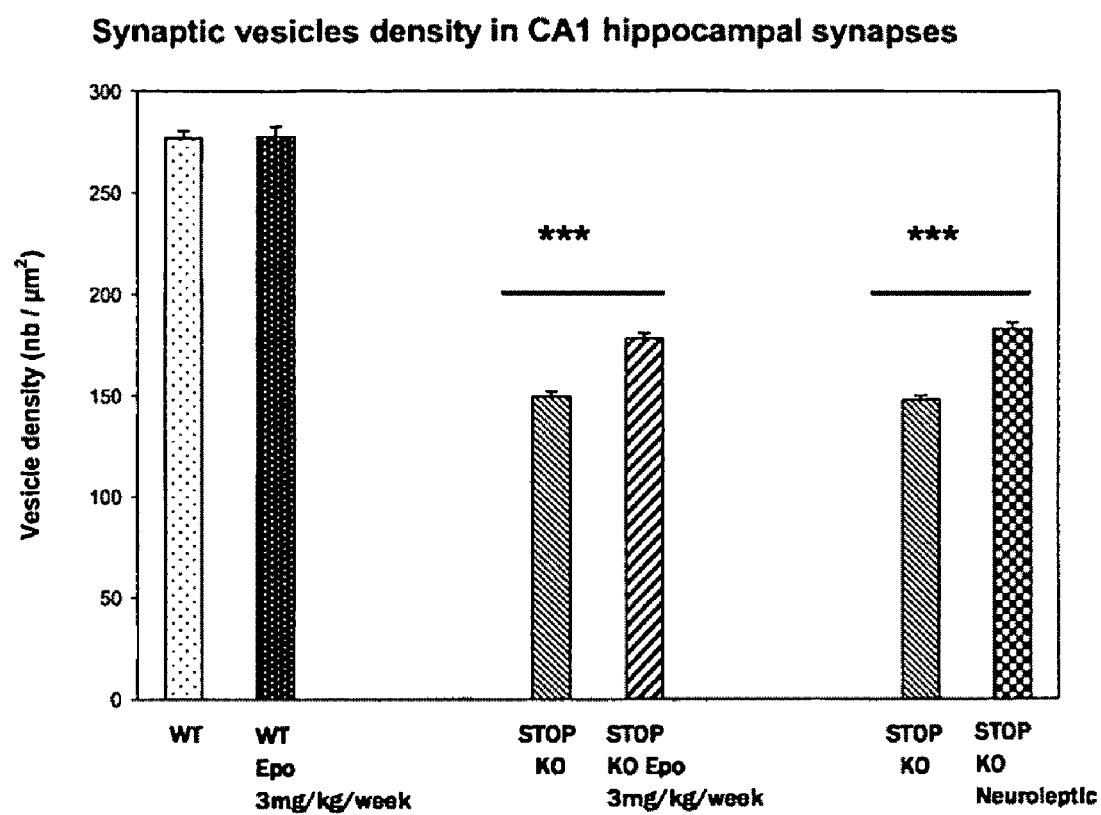
FIG. 5 is a graph illustrating quantitative analysis of synaptic vesicle density in CA1 hippocampal synapses of mice treated or not with epothilone D at a dose of 3 mg/kg/week or with neuroleptics.

After epothilone D treatment, the synaptic vesicle density increased in STOP KO mice (FIG. 5). This increase represented 20% of the vesicle density observed in the absence of treatment and was highly significant (p<0.001). This increase of the vesicle number after epothilone treatment was within the same range as the one observed in parallel experiments using hippocampal sections from 3 STOP KO mice either untreated or treated with neuroleptics (FIG. 5).

The invention claimed is:

1. A method of treating schizophrenia in a human patient, comprising administering to the patient a therapeutic effective amount of an epothilone or pharmaceutically acceptable salt thereof.

2. Method according to claim 1, wherein the epothilone is a compound of formula (I) or a pharmaceutically acceptable salt thereof:

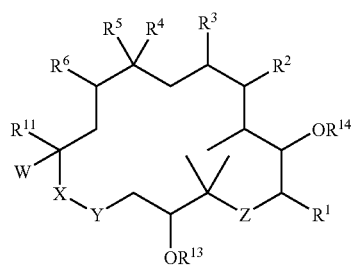

(I)

wherein:
- $R^1$ represents H, alkyl, alkenyl or alkynyl in $C_1$-$C_6$, aryl in $C_6$-$C_{10}$, or aralkyl in $C_7$-$C_{15}$,
- $R^2$, $R^3$ each represents H or form together a C=C double bond,
- $R^4$ represents H, a $C_1$-$C_6$-alkyl, or a fluoro substituted $C_1$-$C_6$ alkyl,
- $R^5$ and $R^6$ form a C=C double bond or a three-member ring including O, S, $NR^7$, or $CR^8R^9$ where:
  - $R^7$ is $C(O)R^{10}$ or $SO_2R^{10}$, and
  - $R^8$, $R^9$, and $R^{10}$ each independently represent H, a halogen, a $C_1$-$C_6$ alkyl, a $C_6$-$C_{10}$ aryl, or a $C_7$-$C_{15}$ alkaryl,
- $R^{11}$ represents H, a $C_1$-$C_6$ alkyl, a $C_6$-$C_{10}$ aryl, or a $C_7$-$C_{15}$ alkaryl,
- W represents $C(R^{12})$=CH, $C(R^{12})$=C(CH$_3$), $C(R^{12})$=CF or a bicyclic aromatic/heteroaromatic radical, with $R^{12}$ representing a heteroaromatic radical,
- X—Y represents O—C(=O), O—CH$_2$, CH$_2$—O, or CH$_2$—C(=O),
- Z represents C=O, S, S=O, or $SO_2$, and
- $R^{13}$ and $R^{14}$ represents independently from each other H, $C_1$-$C_6$-alkyl, (CO)$R^{15}$, or $C_{1-4}$-trialkylsilyl, with $R^{15}$ being H, a $C_1$-$C_6$-alkyl, or a fluoro substituted $C_1$-$C_6$-alkyl.

3. Method according to claim 1, wherein the epothilone is a compound of following formula (II) or a pharmaceutically acceptable salt thereof:

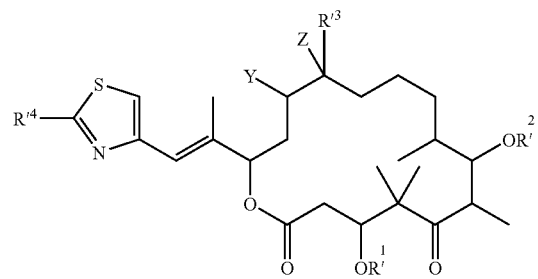

(II)

wherein:
- $R'^4$ represents a $C_1$-$C_6$ alkyl or substituted $C_1$-$C_6$ alkyl with substituents selected from the group consisting of F, Cl, Br, I, —NCO, —NCS, —N$_3$, NH$_2$, OH, O—(C$_1$-C$_6$)-acyl, O—(C$_1$-C$_6$)-alkyl, and O-benzoyl,
- $R'^1$ and $R'^2$ are independently from each other H, a $C_1$-$C_6$-alkyl, (CO)$R'^5$ with $R'^5$ being H, a $C_1$-$C_6$-alkyl, a $C_1$-$C_6$-fluoroalkyl, or a $C_{1-4}$-trialkylsilyl,
- $R'^3$ represents H, $C_1$-$C_6$-alkyl, or a halogen substituted $C_1$-$C_6$-alkyl, and
- Y and Z form either a C=C double bond or are an O atom of an epoxide.

4. Method according to claim 3, wherein $R'^1$, $R'^2$, and $R'^3$ represents independently from each other, H, a $C_1$-$C_6$-alkyl, or a $C_1$-$C_6$ fluoroalkyl.

5. Method according to claim 1, wherein epothilone is at least a natural epothilone A or B represented by the following structural formulas:

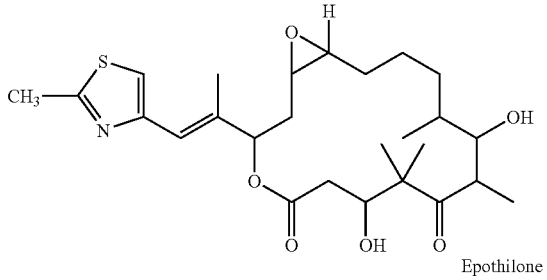

Epothilone A

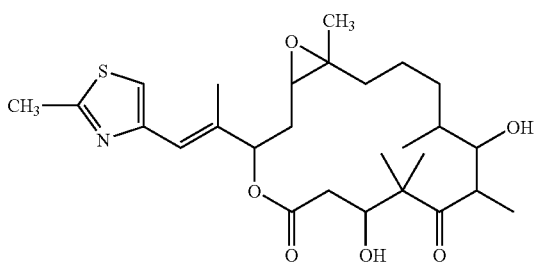

Epothilone B or a pharmaceutically acceptable salt thereof.

6. Method according to claim 1, wherein epothilone is at least one synthetic epothilone C, D, E or F represented by the following structural formulas:

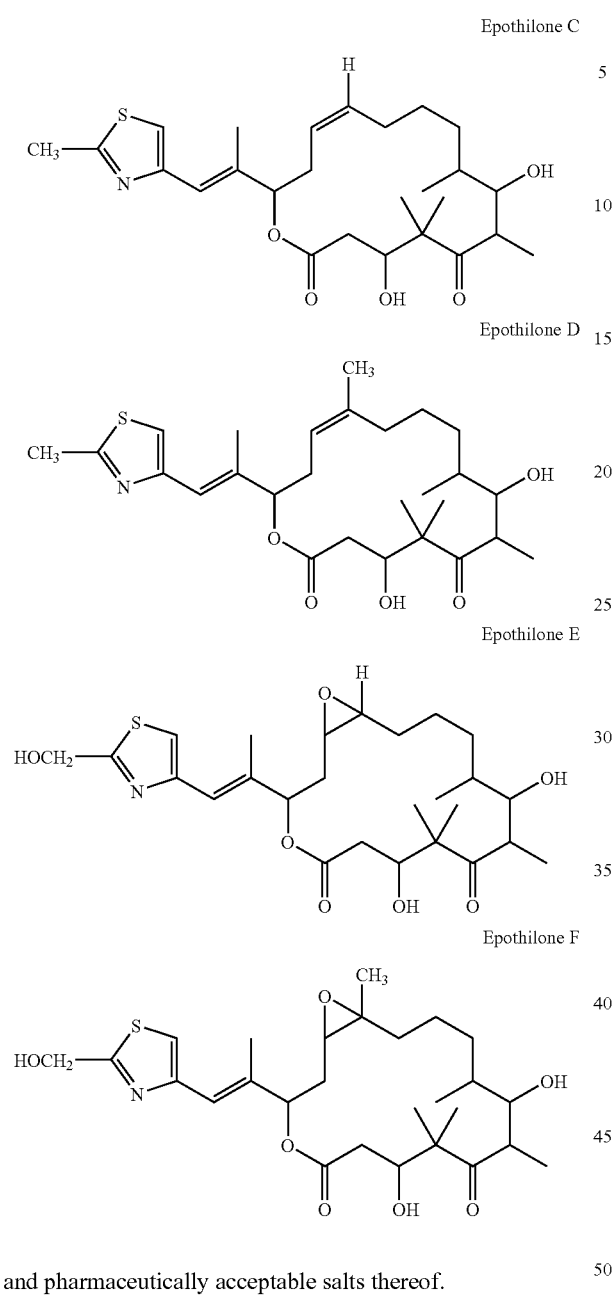

and pharmaceutically acceptable salts thereof.

7. Method according to claim 1, wherein epothilone is at least one synthetic epothilone represented by the following structural formulas:

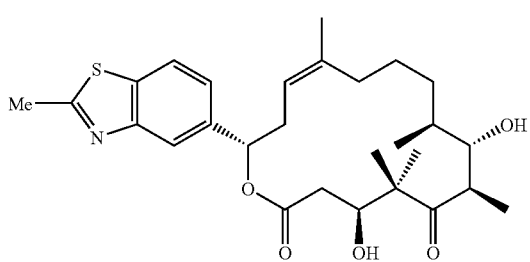

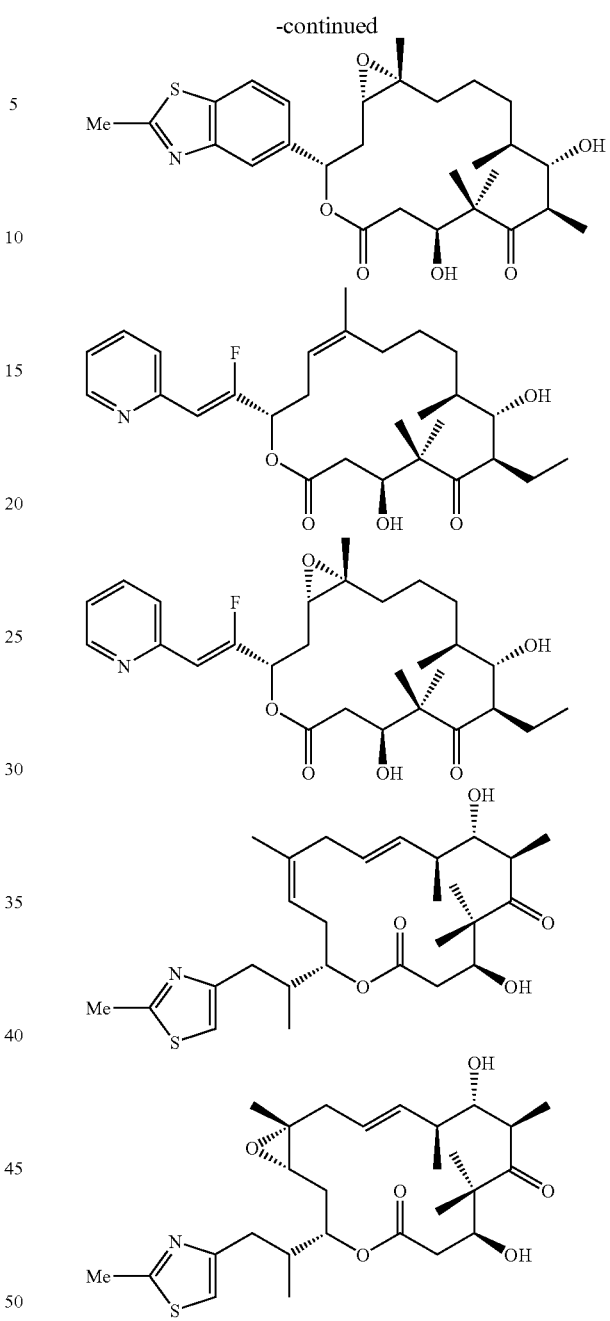

8. Method according to any claim 1, wherein the epothilone or pharmaceutically acceptable salt thereof is used at a therapeutically effective amount from 0.01 mg/Kg/dose to 100 mg/Kg/dose.

9. Method according to claim 1, wherein the epothilone or pharmaceutically acceptable salt thereof is administered in a pharmaceutical composition comprising at least a pharmaceutically acceptable carrier.

10. Method according to claim 1, wherein the epothilone is synthetic epothilone D or a pharmaceutical salt thereof.

11. Method according to claim 2, wherein $R^4$ represents $CH_3$, $CF_3$, or $CFH_2$.

12. Method according to claim 2, wherein $R^{11}$ represents H.

13. Method according to claim 11, wherein $R^{11}$ represents H.

14. Method according to claim 2, wherein W represents a 2-methylbenzothiazol-5-yl radical, a 2-methylbenzoxazol-5-yl radical, or a quinolin-7-yl radical.

15. Method according to claim 11, wherein W represents a 2-methylbenzothiazol-5-yl radical, a 2-methylbenzoxazol-5-yl radical, or a quinolin-7-yl radical.

16. Method according to claim 12, wherein W represents a 2-methylbenzothiazol-5-yl radical, a 2-methylbenzoxazol-5-yl radical, or a quinolin-7-yl radical.

17. Method according to claim 13, wherein W represents a 2-methylbenzothiazol-5-yl radical, a 2-methylbenzoxazol-5-yl radical, or a quinolin-7-yl radical.

18. Method according to claim 2, wherein W represents $C(R^{12})$=CH, $C(R^{12})$=$C(CH_3)$, or $C(R^{12})$=CF, where $R^{12}$ represents a 2-pyridinyl, a 2-substituted thiazol-4-yl, or a 2-substituted oxazol-4-yl radical with substitution in the 2-position by
   $C_1$-$C_6$ alkyl,
   CN,
   $N_3$,
   S—$C_1$-$C_4$-alkyl,
   O—$C_1$-$C_6$-alkyl, or
   $C_1$-$C_6$-alkyl substituted by OH, amino, halogen, —NCO, —NCS, —$N_3$, O—($C_1$-$C_6$)-acyl, O—($C_1$-$C_6$)-alkyl, or O-benzoyl.

19. Method according to claim 11, wherein W represents $C(R^{12})$=CH, $C(R^{12})$=$C(CH_3)$, or $C(R^{12})$=CF, where $R^{12}$ represents a 2-pyridinyl, a 2-substituted thiazol-4-yl, or a 2-substituted oxazol-4-yl radical with substitution in the 2-position by
   $C_1$-$C_6$ alkyl,
   CN,
   $N_3$,
   S—$C_1$-$C_4$-alkyl,
   O—$C_1$-$C_6$-alkyl, or
   $C_1$-$C_6$-alkyl substituted by OH, amino, halogen, —NCO, —NCS, —$N_3$, O—($C_1$-$C_6$)-acyl, O—($C_1$-$C_6$)-alkyl, or O-benzoyl.

20. Method according to claim 12, wherein W represents $C(R^{12})$=CH, $C(R^{12})$=$C(CH_3)$, or $C(R^{12})$=CF, where $R^{12}$ represents a 2-pyridinyl, a 2-substituted thiazol-4-yl, or a 2-substituted oxazol-4-yl radical with substitution in the 2-position by
   $C_1$-$C_6$ alkyl,
   CN,
   $N_3$,
   S—$C_1$-$C_4$-alkyl,
   O—$C_1$-$C_6$-alkyl, or
   $C_1$-$C_6$-alkyl substituted by OH, amino, halogen, —NCO, —NCS, —$N_3$, O—($C_1$-$C_6$)-acyl, O—($C_1$-$C_6$)-alkyl, or O-benzoyl.

21. Method according to claim 13, wherein W represents $C(R^{12})$=CH, $C(R^{12})$=$C(CH_3)$, or $C(R^{12})$=CF, where $R^{12}$ represents a 2-pyridinyl, a 2-substituted thiazol-4-yl, or a 2-substituted oxazol-4-yl radical with substitution in the 2-position by
   $C_1$-$C_6$ alkyl,
   CN,
   $N_3$,
   S—$C_1$-$C_4$-alkyl,
   O—$C_1$-$C_6$-alkyl, or
   $C_1$-$C_6$-alkyl substituted by OH, amino, halogen, —NCO, —NCS, —$N_3$, O—($C_1$-$C_6$)-acyl, O—($C_1$-$C_6$)-alkyl, or O-benzoyl.

22. Method according to claim 2, wherein W represents $C(R^{12})$=CH, $C(R^{12})$=$C(CH_3)$, or $C(R^{12})$=CF, where $R^{12}$ represents a 2-pyridinyl, a 2-substituted thiazol-4-yl, or a 2-substituted oxazol-4-yl radical with substitution in the 2-position by
   $C_1$-$C_6$ alkyl,
   CN,
   $N_3$,
   S—$C_1$-$C_4$-alkyl,
   O—$C_1$-$C_6$-alkyl, or
   $C_1$-$C_6$-alkyl substituted by OH, amino, halogen, —NCO, —NCS, —$N_3$, O—($C_1$-$C_6$)-acyl, O—($C_1$-$C_6$)-alkyl, or O-benzoyl.

23. Method according to claim 4, wherein $R'^1$, $R'^2$, and $R'^3$ each represents independently from each other H, $CH_3$, or $CF_3$.

* * * * *